United States Patent [19]
Hayashi

[11] Patent Number: 6,026,319
[45] Date of Patent: Feb. 15, 2000

[54] FLUORESCENCE DETECTING SYSTEM

[75] Inventor: Katsumi Hayashi, Kanagawa-Ken, Japan

[73] Assignee: Fuji Photo Film Co., Ltd., Kanagawa-ken, Japan

[21] Appl. No.: 09/023,203

[22] Filed: Feb. 13, 1998

[30] Foreign Application Priority Data

Feb. 13, 1997 [JP] Japan .................................. 9-028927

[51] Int. Cl.[7] ........................................................ A61B 5/00
[52] U.S. Cl. ............................................ 600/476; 600/478
[58] Field of Search .................................. 600/310, 476, 600/477, 478; 436/164; 356/317, 318, 319

[56] References Cited

U.S. PATENT DOCUMENTS

| | | | |
|---|---|---|---|
| 4,768,513 | 9/1988 | Suzuki .................................. | 128/634 |
| 5,042,494 | 8/1991 | Alfano .................................. | 128/665 |
| 5,348,018 | 9/1994 | Alfano et al. .......................... | 128/665 |
| 5,456,252 | 10/1995 | Vari et al. ............................. | 128/633 |
| 5,467,767 | 11/1995 | Alfano et al. .......................... | 128/665 |
| 5,507,287 | 4/1996 | Palcic et al. ........................... | 128/633 |
| 5,590,660 | 1/1997 | MacAulay et al. ..................... | 128/664 |
| 5,647,368 | 7/1997 | Zeng et al. ............................. | 128/665 |
| 5,769,792 | 6/1998 | Palcic et al. ........................... | 600/477 |
| 5,827,190 | 10/1998 | Palcic et al. ........................... | 600/476 |
| 5,833,617 | 11/1998 | Hayashi ................................. | 600/476 |
| 5,849,595 | 12/1998 | Alfano et al. .......................... | 436/164 |

*Primary Examiner*—J. Jastrzab
*Assistant Examiner*—Eleni Mantis Mercader
*Attorney, Agent, or Firm*—Sughrue, Mion, Zinn, Macpeak & Seas, PLLC

[57] ABSTRACT

A fluorescence detecting system detects auto fluorescence emitted from an intrinsic pigment in a part of an organism. An excitation light projector intermittently projects onto the part excitation light in the wavelength range which can excite the intrinsic pigment of the organism to emit auto fluorescence. A fluorescence detector extracts an auto fluorescence component in a desired wavelength range from auto fluorescence emitted from the pigment. A net auto fluorescence component in the desired wavelength range is obtained by subtracting a base line component in the desired wavelength range the fluorescence detector detects when the part of the organism is not exposed to the excitation light from a gross auto fluorescence component in the desired wavelength range the fluorescence detector detects when the part of the organism is exposed to the excitation light. A divider carries out a division between a first part of the net auto fluorescence component in the desired wavelength range and a second part of the same.

20 Claims, 5 Drawing Sheets

FLUORESCENCE DETECTING SYSTEM

BACKGROUND OF THE INVENTION

FIELD OF THE INVENTION

This invention relates to a fluorescence detecting system in which a photosensitive material, which has an affinity to tumors and emits fluorescence when excited by light, is first administered to an organism, they excitation light is projected onto the part to be observed of the organism, and then the intensity of the fluorescence emitted from the photosensitive material and pigment inherent to the organism is measured, or in which the intensity of auto fluorescence emitted from pigment without administering any photosensitive material is measured. The presence of a tumor is diagnosed on the basis of the intensity of the fluorescence measured.

DESCRIPTION OF THE RELATED ART

There have been made various investigations on photodynamic diagnosis. The photodynamic diagnosis is a technique in which a photosensitive material (ATX-S10, 5-ALA, NPe6, HAT-D01, Photofrin-2 or the like), which has an affinity to tumors and emits fluorescence when excited by light, is first administered to the tumor as a fluorescence diagnosis agent, them excitation light having a wavelength in the exciting wavelength range of the photosensitive material is projected onto the tumor to cause the fluorescence of the diagnosis agent collected in the tumor, and the tumor is diagnosed on the basis of an image which is formed by the fluorescence and shows the location and the area of infiltration of the diseased part.

A fluorescence diagnosis system for carrying out such photodynamic diagnosis is disclosed, for instance, in Japanese Patent Publication No. 63(1988)-9464 and Japanese Unexamined Patent Publication Nos. 1(1989)-136630 and 7(1995)-59783. The fluorescence diagnosis system basically comprises an excitation light projecting means which projects excitation light having a wavelength in the exciting wavelength range of the photosensitive material onto an organism, an image taking means which takes a fluorescence image of the organism formed by fluorescence emitted from the photosensitive material and an image display means which displays a fluorescence image on the basis of output of the image taking means. Such a fluorescence diagnosis system is generally incorporated in an endoscope or an operative microscope.

Further there has been proposed a technique of diagnosing tumors in which excitation light having a wavelength in the exciting wavelength range of pigment inherent to an organism is projected onto the organism without administering any photosensitive material to the organism and an image of the location and the area of infiltration of the diseased part is displayed on the basis of auto fluorescence emitted from the pigment, and a tumor is diagnosed on the basis of the fluorescence image.

Further there has been known a fluorescence diagnosis system in which, without taking a two-dimensional fluorescence image, the intensity of fluorescence is detected for each point on an organism and whether the point is tumor-bearing is determined according to the intensity of fluorescence. See, for instance, Japanese Unexamined Patent Publication No. 9(1997)-149891.

In such a fluorescence diagnosis system, since the surface of a part of an organism is generally uneven, the distance between the excitation light projecting means and the part to be observed differs from point to point and accordingly illuminance of the excitation light generally differs from point to point. The intensity of fluorescence is generally proportional to the illuminance of the excitation light and the illuminance of the excitation light reduces in reverse proportion to the square of the distance from the light source. Accordingly, there are cases where a normal part near to the light source emits fluorescence stronger than that emitted from a diseased part remote from the light source or fluorescence from a diseased part positioned inclined to the excitation light is extremely weakened. Thus nonuniformity of illuminance of the excitation light can lead to misdiagnosis.

In order to compensate for the change in intensity of fluorescence due to difference in distance from the light source, there have been proposed fluorescence diagnosis systems such as disclosed in Japanese Unexamined Patent Publication No. 62(1987)-247232, Japanese Patent Publication No. 3(1991)-58729 and the like. In the fluorescence diagnosis system disclosed in the former patent publication, excitation light is projected onto a part of an organism which has been given a photosensitive material having a strong affinity to a diseased part, then emitted fluorescence and an reflected excitation light are detected and image processing operation is carried out on the basis of a division between the fluorescence component and the reflected light component. By such a division, terms related to the distance from the light source can be cancelled. However since there remains a term related to the reflectance of the part exposed to the excitation light in the result of the division, there still remains a problem that a fluorescence image accurately reflecting the distribution of the fluorescence diagnosis agent cannot be obtained.

In the system disclosed in "FLUORESCENCE IMAGING OF EARLY LUNG CANCER" (Annual International Conference of the IEEE Engineering and Biology Society. Vol. 12, No.3, 1990), auto fluorescence emitted from the intrinsic pigment of a part to be observed in an organism is divided into a component having a wavelength in a green region (which will be referred to as "the green region component G", hereinbelow) and a component having a wavelength in a red region (which will be referred to as "the red region component R", hereinbelow), and carries out an image processing operation on the basis of division between the red region component R and the green region component G, and a result of the division is displayed. That is, since in a spectrum of auto fluorescence emitted from a diseased part, the intensity of the green region is extremely weaker than that in a spectrum of auto fluorescence emitted from a normal part, the reduction rate of the green region component G is much larger than of the red region component R in the auto fluorescence emitted from the diseased part. Accordingly by division of R/G, the fluorescence from the diseased part can be specifically extracted and an image can be formed on the basis of the extracted fluorescence. In the system, though the term of fluorescence intensity depending on the distances between the excitation light source and the part to be observed of the organism and between the fluorescence receiving section and the part to be observed of the organism can be cancelled, there is a problem that the S/N ratio becomes extremely low due to an extremely weak auto fluorescence at the diseased part.

In "Fluorescence Image Diagnosis of Cancer Using Red/Green Ratio" reported in 16-th Conference of Japanese Laser Medical Society, 1995 (Tokyo Medical College, Hamamatsu Photonix), it is proposed to strengthen red fluorescence at a diseased part by use of a fluorescence diagnosis agent which is accumulated in a diseased part and emits red fluorescence, and then to carry out operation of R/G. In this system, there can be obtained a fluorescence image in which the intensity of fluorescence from the diseased part is increased as compared with the system described in the aforesaid "FLUORESCENCE IMAGING OF EARLY LUNG CANCER".

By use of operation of R/G, the term of fluorescence intensity depending on the distances between the excitation light source and the part to be observed of the organism and between the fluorescence receiving section and the part to be observed of the organism can be cancelled.

However, since the green auto fluorescence at the diseased part is extremely weak, there still remains a problem that operation of r/G sometimes results in division of a value by 0, which is apt to lead to operation errors. This problem may be overcome by carrying out a division with a whole auto fluorescence component in a wavelength range ranging from a green region to a red region or a sum fluorescence component of a red region component and a green region component employed as a divisor.

However since a base line component due to, background light, electrical drift and the like is generally superimposed on the fluorescence component and adds offset to a fluorescence spectrum, the base line component causes error. Accordingly, even if a division for correcting the intensity of the fluorescence is carried out, the base line component deteriorates the effect of the correction.

SUMMARY OF THE INVENTION

In view of the foregoing observations and description, the primary object of the present invention is to provide a fluorescence detecting system in which the intensity of fluorescence which depends upon the distances between the excitation light source and the part to be observed and between the fluorescence receiving means and the part to be observed can be corrected so that operation errors cannot occur.

In accordance with a first aspect of the present invention, there is provided a fluorescence detecting system for detecting auto fluorescence emitted from an intrinsic pigment in a part of an organism to be observed upon excitation by excitation light without giving any photosensitive material (fluorescence diagnosis agent) to the part, comprising an excitation light projecting means which intermittently projects onto the part to be observed excitation light in the wavelength range which can excite the intrinsic pigment of the organism to emit auto fluorescence (for instance by use of a rotary disc having a hole or a liquid crystal shutter or by turning on and off a light source), a fluorescence detecting means which extracts an auto fluorescence component in a desired wavelength range from auto fluorescence emitted from the pigment, a base line component removing means which obtains a net auto fluorescence component in the desired wavelength range by subtracting a base line component (due to, background light, electrical drift and the like) in the desired wavelength range the fluorescence detecting means detects when the part of the organism is not exposed to the excitation light from a gross auto fluorescence component in the desired wavelength range the fluorescence detecting means detects when the part of the organism is exposed to the excitation light, and a divider means which carries out a division between a first part of the net auto fluorescence component in the desired wavelength range and a second part of the same.

In one embodiment, said fluorescence detecting means detects a whole visible auto fluorescence component in a visible region having a predetermined wavelength range including a first relatively short wavelength range and a first relatively long wavelength range and one of an auto fluorescence component in a second relatively short wavelength range, an auto fluorescence component in a second relatively long wavelength range and a difference fluorescence component between the auto fluorescence components in said second relatively short wavelength range and in said second relatively long wavelength range, and said first part of the net auto fluorescence component is obtained from said one auto fluorescence component and said second part of the net auto fluorescence component is obtained from the whole visible auto fluorescence component.

In another embodiment, said fluorescence detecting means detects a sum fluorescence component of an auto fluorescence component in a first short wavelength range and an auto fluorescence component in a first relatively long wavelength range, and one of an auto fluorescence component in a second relatively short wavelength range, an auto fluorescence component in a second relatively long wavelength range and a difference fluorescence component between the auto fluorescence components in said second relatively short wavelength range and in said second relatively long wavelength range, and said first part of the net auto fluorescence component is obtained from said one auto fluorescence component and said second part of the net auto fluorescence component is obtained from the sum auto fluorescence component.

The first and second relatively short wavelength ranges may be either the same wavelength range or different wavelength ranges. The first and second relatively long wavelength ranges may be either the same wavelength range or different wavelength ranges. Further the visible region need not include the whole of the first relatively long wavelength range but may include only a part of the first relatively long wavelength range.

Further the fluorescence detecting means may detect the aforesaid fluorescence component in any manner. For example, the desired fluorescence component may be directly extracted by separating from the fluorescence as emitted from the pigment by use of an optical filter or the like, or may be extracted by separating the fluorescence component in a predetermined wavelength range partly different from a desired fluorescence component from the auto fluorescence as emitted from the pigment and carrying out an operation processing such as addition and/or subtraction on the separated fluorescence component. In accordance with a second aspect of the present invention, there is provided a fluorescence detecting system for detecting fluorescence emitted from a part of an organism to be observed which has been given a fluorescent photosensitive material, comprising an excitation light projecting means which intermittently projects onto the part to be observed excitation light in the wavelength range which can excite an intrinsic pigment of the organism and said fluorescent photosensitive material to emit fluorescence (for instance by use of a rotary disc having a hole or a liquid crystal shutter or by turning on and off a light source), a fluorescence detecting means which extracts a fluorescence component in a desired wavelength range from fluorescence emitted from the pigment and the photosensitive material, a base line component removing means which obtains a net fluorescence component in the desired wavelength range by subtracting a base line component (due to, background light, electrical drift and the like) in the desired wavelength range the fluorescence detecting means detects when the part of the organism is not exposed to the excitation light from a gross fluorescence component in the desired wavelength range which the fluorescence detecting means detects when the part of the organism is exposed to the excitation light, and a divider means which carries out a division between a first part of the net fluorescence component in the desired wavelength range and a second part of the same.

In one embodiment, said fluorescence detecting means detects a whole visible fluorescence component in a visible region having a predetermined wavelength range including a first wavelength range of extrinsic fluorescence emitted from the photosensitive material and a first wavelength range of auto fluorescence emitted from the pigment and one of a fluorescence component in a second wavelength range of the extrinsic fluorescence, a fluorescence component in a second wavelength range of the auto fluorescence and a difference fluorescence component between the fluorescence components in said second wavelength range of the extrinsic fluorescence and in said second wavelength range of the auto fluorescence, and said first part of the net fluorescence component is obtained from said one fluorescence component and said second part of the net fluorescence component is obtained from the whole visible fluorescence component.

In another embodiment, said fluorescence detecting means detects a sum fluorescence component of a fluorescence component in a first wavelength range of extrinsic fluorescence emitted from the photosensitive material and fluorescence component in a first wavelength range of auto fluorescence emitted from the pigment and one of a fluorescence component in a second wavelength range of the extrinsix fluorescence, a fluorescence component in a second wavelength range of the auto fluorescence and a difference fluorescence component between the fluorescence components in said second wavelength range of the extrinsic fluorescence and in said second wavelength range of the auto fluorescence, and said first part of the net fluorescence component is obtained from said one fluorescence component and said second part of the net fluorescence component is obtained from the sum fluorescence component.

Also in this case, the first and second wavelength ranges may be either the same wavelength range or different wavelength ranges. Further the visible region need not include the whole of the first wavelength range but may include only a part of the first wavelength range.

In both the aforesaid fluorescence detecting systems of the present invention, the fluorescence detecting means need not be limited to those which detect the intensity of fluorescence for each point on the part to be observed but may be those which two-dimensionally detect the fluorescence emitted from the part to be observed and take a fluorescence image of the part.

In the fluorescence detecting systems of the present invention, since a net fluorescence component is obtained by subtracting a base line component (due to, background light, electrical drift and the like) which the fluorescence detecting means detects when the part of the organism is not exposed to the excitation light from a gross fluorescence component which the fluorescence detecting means detects when the part of the organism is exposed to the excitation light, and a division is carried out on the basis of the net fluorescence component, occurrence of operation error due to the base line component can be prevented and the fluctuation in intensity of fluorescence due to difference in distance between the excitation light source and the part to be observed can be stably removed.

Further by carrying out a division with a net visible whole fluorescence component in a wavelength range ranging from a green region to a red region or a sum fluorescence component of a net red region component and a net green region component employed as a divisor, the intensity of the fluorescence can be corrected without possibility of generating operational error due to the base line component or due to a division of a value by 0.

DESCRIPTION OF THE PREFERRED EMBODIMENT

Figure 1:
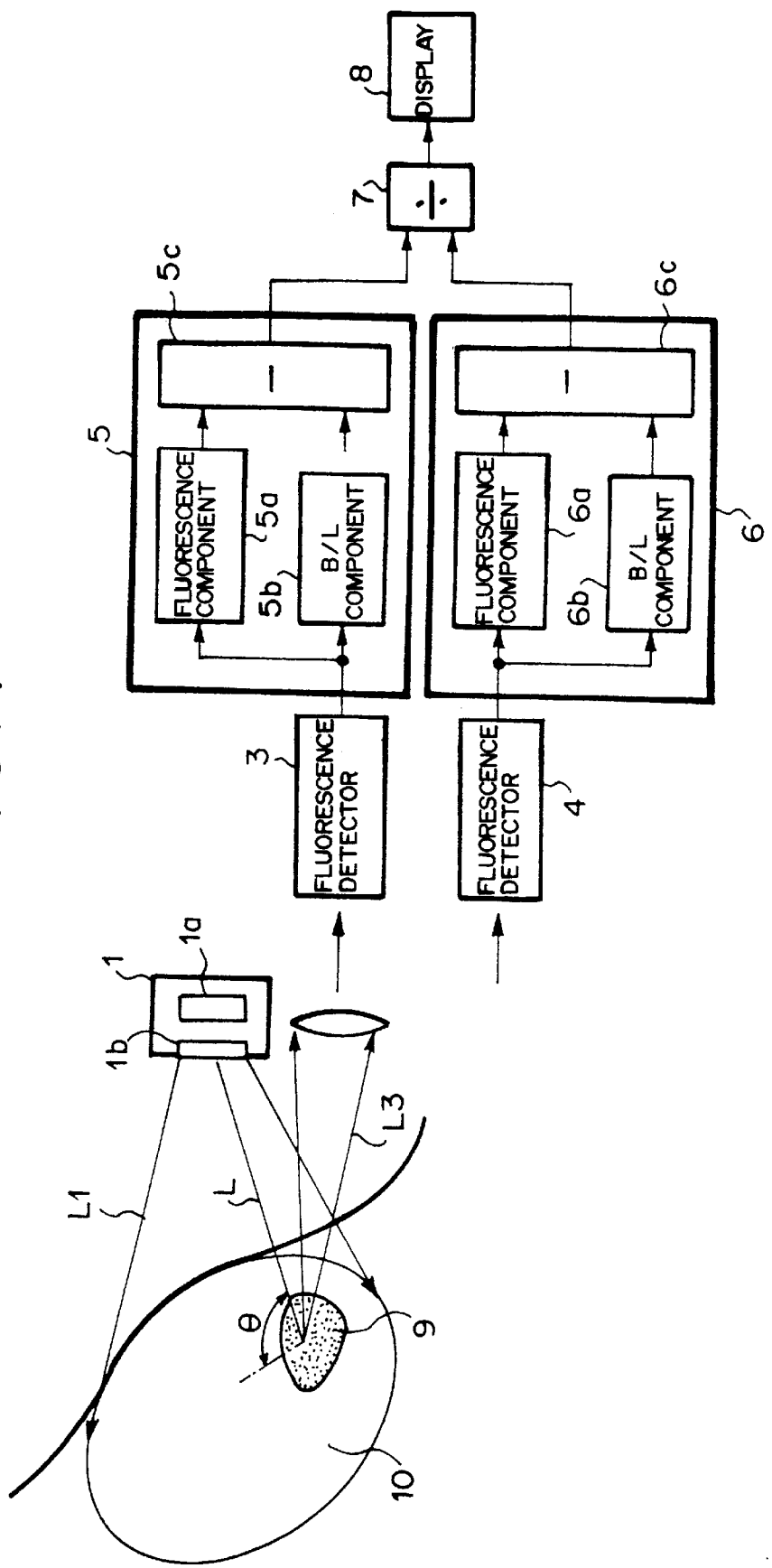
FIG. 1 is a schematic view showing a basic arrangement of a fluorescence detecting system of the present invention.

As shown in FIG. 1, the fluorescence detecting system of the present invention basically comprises an excitation light projecting means 1 which intermittently projects excitation light L1 onto a part 10 to be observed (will be referred to as "the diagnostic part", hereinbelow) of an organism, first and second fluorescence detecting means 3 and 4 which separate fluorescence L3 emitted from the diagnostic part 10 into desired wavelength ranges and extracts fluorescence components in the desired wavelength ranges, first and second base line component removing means 5 and 6, and a divider means 7 which carries out a division on the basis of the outputs of the first and second base line component removing means 5 and 6. The output of the divider means 7 is input into a display means 8 which displays a visible image.

The excitation light projecting means 1 comprises an excitation light source 1a which emits the excitation light L1 and an excitation light intermitting means 1a such as a rotary disc having a hole, a liquid crystal shutter or the like which causes the excitation light L1 emitted from the light source 1a to be intermittently projected onto the, diagnostic part 10. The first base line component removing means 5 comprises a memory 5a which stores a fluorescence component which the first fluorescence detecting means 3 detects when the excitation light L1 is projected onto the diagnostic part 10 and a memory 5b which stores a background light component which the first fluorescence detecting means 3 detects when the excitation light L1 is intermitted and a subtractor 5c which subtracts output of one of the memories 5a and 5b from the output of the other. The second base line component removing means 6 comprises a memory 6a which stores a fluorescence component which the second fluorescence detecting means 4 detects when the excitation light L1 is projected onto the diagnostic part 10 and a memory 6b which stores a background light component which the second fluorescence detecting means 4 detects when the excitation light L1 is intermitted and a subtractor 6c which subtracts output of one of the memories 6a and 6b from the output of the other.

A method of correcting the intensity of fluorescence which depends upon the distances between the excitation light projecting means 1 and each point of the diagnostic part 10 and between each point of the diagnostic part 10 and the fluorescence receiving section (the first and second fluorescence detecting means 3 and 4) as well as removing the influence of the base line component will be described in detail, hereinbelow.

First a description will be made on a case where auto fluorescence emitted from intrinsic pigment in the diagnostic part 10 upon excitation by the excitation light L1 without giving any fluorescence diagnosis agent to the diagnostic part 10 is detected and a division is carried out between an auto fluorescence component in a relatively short wavelength range in a visible region having a predetermined wavelength range (e.g., a green region component G, will be referred to as "the short wavelength component", hereinbelow) and a whole auto fluorescence component in a relatively long wavelength range in the visible region (e.g., red region component R, will be referred to as "the long wavelength component", hereinbelow).

The auto fluorescence L3 emitted from the pigment in the diagnostic part 10 is separated into the short wavelength component and the long wavelength component by a dichroic mirror or the like and the first and second fluorescence detecting means 3 and 4 respectively detect the long wavelength component and the short wavelength component. The long wavelength component which the first fluorescence detecting means 3 detects when the excitation light L1 is projected onto the diagnostic part 10 is stored in the memory 5a and the basetime component that the first fluorescence detecting means 3 detects when the excitation light L1 is intermitted is stored in the memory 5b. The short wavelength component which the second fluorescence detecting means 4 detects when the excitation light L1 is projected onto the diagnostic part 10 is stored in the memory 6a and the basetime component that the second fluorescence detecting means 4 detects when the excitation light L1 is intermitted is stored in the memory 6b.

The excitation light L1 of a wavelength $\lambda_{ex}$ is continuously emitted from the excitation light source 1a and intermittently projected onto the diagnostic part 10 including a diseased part 11 by the excitation light intermitting means 1a. Though the excitation light source 1a itself may be turned on and off without use of the excitation light intermitting means 1a, it is preferred from the viewpoint of the service life of the light source 1a and the like that the excitation light source 1a be kept on and the excitation light L1 be intermitted by the excitation light intermitting means 1a.

Auto fluorescence L3 is emitted from the diagnostic part 10 by an intrinsic pigment and the short wavelength component of the auto fluorescence L3 is detected by the first fluorescence detecting means 3 and the long wavelength component is detected by the second fluorescence detecting means 4. The first and second fluorescence detecting means 3 and 4 may be either a photodetector such as a photodiode which detects the auto fluorescence L3 from point to point or those such as a CCD image taking device which two-dimensionally detects the auto fluorescence L3 and forms a fluorescence image.

Figure 2:
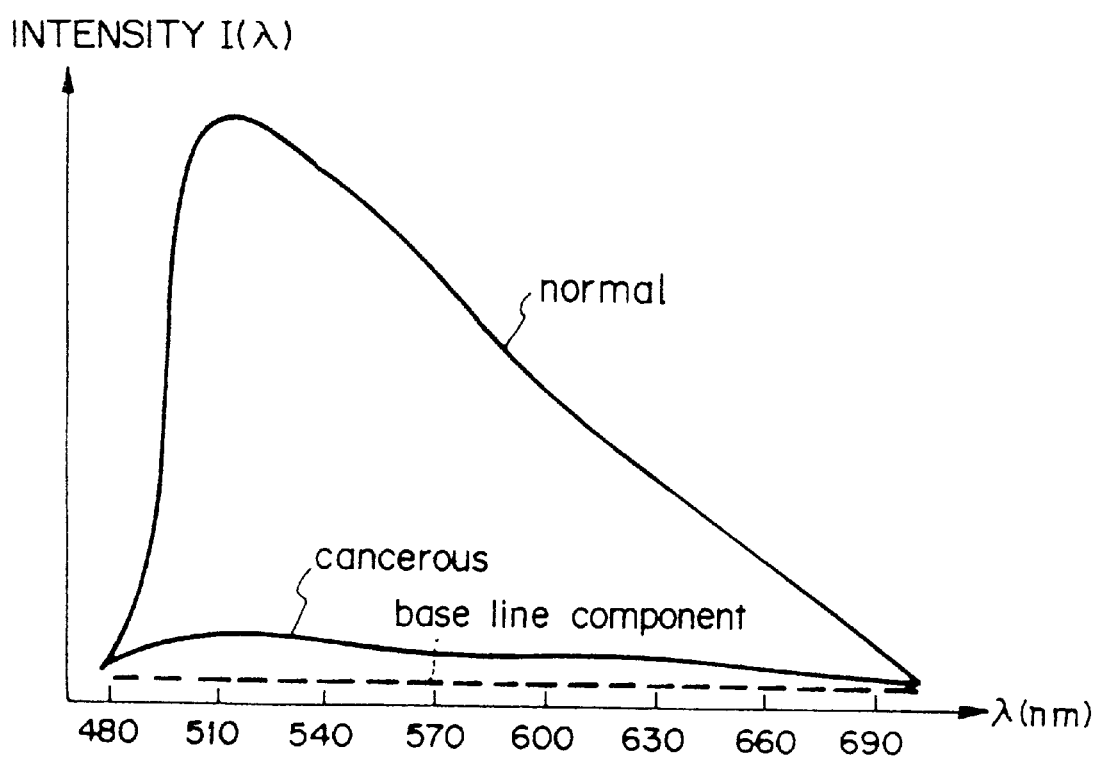
FIG. 2 is a view for illustrating a spectrum of auto fluorescence.

When the diagnostic part 10 is exposed to the excitation light L1, the diagnostic part 10 emits auto fluorescence L3 having a spectrum such as shown in FIG. 2. The auto fluorescence L3 is considered to include fluorescence emitted from various pigment in the organism such as FAD, collagen, fibronectin, porphyrin and the like. As shown in FIG. 2, the spectrum of the auto fluorescence L3 emitted from a normal part differs from that of auto fluorescence L3 emitted from a diseased part both in magnitude and shape, the reason for which has not been found. The spectrum of the auto fluorescence L3 from the normal part is large on the whole whereas the auto fluorescence L3 from the diseased part is weak on the whole. The degree by which the auto fluorescence L3 from the diseased part is weakened is lower in the fluorescence component having wavelengths longer than the red region as compared with the fluorescence component in the blue to green region. That is, the ratio of the near green fluorescence component to the near red fluorescence component differs between the normal part and the diseased part. Accordingly the diseased part can be distinguished from the normal part on the basis of the aforesaid ratio of the auto fluorescence L3.

The first and second fluorescence detecting means 3 and 4 detect the base line component, due to leakage of the excitation light, background light, electrical drift and the like, even when the excitation light L1 is cut. Accordingly the spectrum obtained when the diagnostic part 10 is exposed to the excitation light L1 includes the base line component superimposed on the net fluorescence component. In this embodiment, the base line component is removed in the following manner. Means of the symbols used hereinbelow are as follows.

$\lambda_{ex}$: the wavelength of the excitation light L1, $I\lambda_{ex}$: the intensity of the excitation light L1 at the diagnostic part 10 which depends upon the distance L between the excitation light source 1a and the diagnostic part 10, the power P of the excitation light source 1a and the angle a at which the light bundle of the excitation light L1 impinges upon the diagnostic part 10, $I\lambda_{ex}=I\lambda_{ex}(L, P, \theta)$, n: the apparent density of the auto fluorescence molecules which contribute to the long wavelength component (Though the auto fluorescence molecules which contribute to auto fluorescence are considered to be of a plurality of kinds, here they may be considered to be of a single kind. In this sense, the term "apparent" is used in this specification.), N: the apparent density of the auto fluorescence molecules which contribute to the short wavelength component, M: the apparent density of the auto fluorescence molecules which contribute to the whole visible auto fluorescence component, $k\lambda_1$: a constant which depends upon the wavelength $\lambda_{ex}$ of the excitation light L1 and the apparent density N of the auto fluorescence molecules which contribute to the short wavelength component, $k\lambda_2$: a constant which depends upon the wavelength $\lambda_{ex}$ of the excitation light L1 and the apparent density n of the auto fluorescence molecules which contribute to the long wavelength component, $k\lambda_3$: a constant which depends upon the wavelength $\lambda_{ex}$ of the excitation light L1 and the apparent density M of the auto fluorescence molecules which contribute to the whole visible auto fluorescence component, $\eta F\lambda_1$: the fluorescence quantum yield to the wavelength $\lambda_{ex}$ of the excitation light L1 of the auto fluorescence molecules which contribute to the short wavelength component, $\eta F\lambda_2$: the fluorescence quantum yield to the wavelength $\lambda_{ex}$ of the excitation light L1 of the auto fluorescence molecules which contribute to the long wavelength component, $\eta F\lambda_3$: the fluorescence quantum yield to the wavelength $\lambda_{ex}$ of the excitation light L1 of the auto fluorescence molecules which contribute to the whole visible auto fluorescence component, $\eta D$: the fluorescence detecting efficiency which depends upon the distance L' between a point on the diagnostic part 10 and the fluorescence detecting system, the aperture D of the fluorescence detecting system and the efficiency $\xi$ of the detector, $\eta D = \eta D (L', \xi, D)$, (though, strictly speaking, the detecting efficiency for the short wavelength component differs from that for the long wavelength component, they may be handled to be approximately equal to each other here), $I_{B1}$: the base line component superimposed on the short wavelength component, $I_{B2}$: the base line component superimposed on the long wavelength component, $I_{B3}$: the base line component superimposed on the whole visible auto fluorescence component.

The short wavelength component $If\lambda_1'$ detected by the second fluorescence detecting means 4 when the diagnostic part 10 is exposed to the excitation light L1 is stored in the memory 6a and the long wavelength component $If\lambda_2'$ detected by the first fluorescence detecting means 3 when the diagnostic part 10 is exposed to the excitation light L1 is stored in the memory 5a. The short wavelength component $If\lambda_1''$ detected by the second fluorescence detecting means 4 when the diagnostic part 10 is not exposed to the excitation light L1 is stored in the memory 6b and the long wavelength component $If\lambda_2''$ detected by the first fluorescence detecting means 3 when the diagnostic part 10 is not exposed to the excitation light L1 is stored in the memory 5b.

The respective components detected by the first and second fluorescence detecting means 3 and 4 are represented as follows.

The apparent short wavelength component $If\lambda_1'$ when the diagnostic part 10 is exposed to the excitation light L1:

$$If\lambda_1' = k\lambda_1 \cdot I\lambda_{ex} \cdot \eta F\lambda_1 \cdot N \cdot \eta D + I_{B1}.$$

The apparent long wavelength range component $If\lambda_2'$ when the diagnostic part 10 is exposed to the excitation light L1:

$$If\lambda_2' = k\lambda_2 \cdot I\lambda_{ex} \cdot \eta F\lambda_2 \cdot n \cdot \eta D + I_{B2}.$$

The apparent short wavelength component $If\lambda_1''$ when the diagnostic part 10 is not exposed to the excitation light Li:

$$If\lambda_1'' = I_{B1}.$$

The apparent long wavelength range component $If\lambda_2''$ when the diagnostic part 10 is not exposed to the excitation light L1: $If\lambda_2'' = I_{B2}$.

The subtracter 6c subtracts the apparent short wavelength component $If\lambda_1''$ when the diagnostic part 10 is not exposed to the excitation light L1 from the apparent short wavelength component $If\lambda_1'$ when the diagnostic part 10 is exposed to the excitation light L1 and obtains a net short wavelength component $If\lambda_1$. The net short wavelength component $if\lambda_1$ is represented as follows.

$$If\lambda_1 = k\lambda_1 \cdot I\lambda_{ex} \cdot \eta F\lambda_1 \cdot N \cdot \eta D$$

The subtracter Sc subtracts the apparent long wavelength component $If\lambda_2''$ when the diagnostic part 10 is not exposed to the excitation light L1 from the apparent long wavelength component $If\lambda_2'$ when the diagnostic part 10 is exposed to the excitation light L1 and obtains a net long wavelength component $If\lambda_2$. The net short wavelength component $If\lambda_2$ is represented as follows.

$$If\lambda_2 = k\lambda_2 \cdot I\lambda_{ex} \cdot \eta F\lambda_2 \cdot n \cdot \eta D$$

Then the divider means 7 divides the net short wavelength component $If\lambda_1$ by the net long wavelength component $If\lambda_2$. That is, $$If\lambda_2 / If\lambda_1 = (k\lambda_2 \cdot \eta F\lambda_2 \cdot \eta) / (k\lambda_1 \cdot \eta F\lambda_1 \cdot N)$$

By this division, the term depending on the distance between the excitation light source 1a and the diagnostic part 10 is cancelled. In the manner described above, the intensity of fluorescence can be effectively corrected even there is a base line component.

Though the above description is made on the case where the auto fluorescence emitted from the diagnostic part 10 which has not been given any fluorescence diagnosis agent is detected, this embodiment can be also applied when the extrinsic fluorescence emitted from the diagnostic part 10 which has been given a fluorescence diagnosis agent is detected. In this case, the above "long wavelength component" should be reread as "extrinsic fluorescence" and the above "short wavelength component" should be reread as "auto fluorescence".

Now a description will be made on a case where auto fluorescence emitted from intrinsic pigment in the diagnostic part 10 upon excitation by the excitation light L1 without giving any fluorescence diagnosis agent to the diagnostic part 10 is detected and a division is carried out between a short wavelength component (e.g., a green component G) and a sum fluorescence component of an auto fluorescence component in a relatively short wavelength range in the visible region and an auto fluorescence component in a relatively long wavelength range in the visible region (e.g., G+R).

The auto fluorescence L3 emitted from the pigment in the diagnostic part 10 is separated into a short wavelength component and a sum fluorescence component of a short wavelength component and a long wavelength component by a dichroic mirror or the like and the first and second fluorescence detecting means 3 and 4 respectively detect the short wavelength component and the sum component. The short wavelength component which the first fluorescence detecting means 3 detects when the excitation light L1 is projected onto the diagnostic part 10 is stored in the memory 5a and that the first fluorescence detecting means 3 detects when the excitation light L1 is intermitted is stored in the memory 5b. The sum fluorescence component which the second fluorescence detecting means 4 detects when the excitation light L1 is projected onto the diagnostic part 10 is stored in the memory 6a and that the second fluorescence detecting means 4 detects when the excitation light L1 is intermitted is stored in the memory 6b.

The means for detecting the short wavelength component and the sum fluorescence component need not be limited to those described above. For example, the desired fluorescence component may be extracted by separating the fluorescence component in a predetermined wavelength range including therein a desired fluorescence component from the auto fluorescence as emitted from the pigment and carrying out an operation processing such as addition and/or subtraction on the separated fluorescence component. More specifically, the auto fluorescence as emitted is separated into a component in a relatively short wavelength range and a component in a relatively long wavelength range and the former and latter components are detected respectively by the first and second fluorescence detecting means 3 and 4. Then the outputs of the first and second fluorescence detecting means 3 and 4 are added to obtain the sum fluorescence component. Otherwise, the auto fluorescence as emitted is separated into a component in a relatively long wavelength range and a sum component of a component in a relatively long wavelength range and a component in a relatively short wavelength range and the former and latter components are detected respectively by the first and second fluorescence detecting means 3 and 4. Then the output of the first fluorescence detecting means 3 is subtracted from the output of the second fluorescence detecting means 4 to obtain the short wavelength component.

The respective components detected by the first and second fluorescence detecting means 3 and 4 are represented as follows.

The apparent short wavelength component $If\lambda_1'$ when the diagnostic part 10 is exposed to the excitation light L1:

$$If\lambda_1' = k\lambda_1 \cdot I\lambda_{ex} \cdot \eta F\lambda_1 \cdot N \cdot \eta D + I_{B1}.$$

The apparent long wavelength range component $If\lambda_2'$ when the diagnostic part 10 is exposed to the excitation light L1:

$$If\lambda_2' = k\lambda_2 \cdot I\lambda_{ex} \cdot \eta F\lambda_2 \cdot n \cdot \eta D + I_{B2}.$$

Accordingly, the sum fluorescence component $If\lambda'$ of the short wavelength component and the long wavelength component when the diagnostic part 10 is exposed to the excitation light L1 is represented as follows.

$$If\lambda' = (k\lambda_1 \cdot I\lambda_{ex} \cdot \eta F\lambda_1 \cdot N \cdot \eta D) + (k\lambda_2 \cdot I\lambda_{ex} \cdot \eta F\lambda_2 \cdot n \cdot \eta D) + I_{B1} + I_{B2}.$$

The apparent short wavelength component $If\lambda_1''$ when the diagnostic part 10 is not exposed to the excitation light L1:

$$If\lambda_1'' = I_{B1}.$$

The apparent long wavelength range component $If\lambda_2''$ when the diagnostic part 10 is not exposed to the excitation light L1: $If\lambda_2'' = I_{B2}$.

Accordingly the sum fluorescence component $If\lambda''$ of the short wavelength component and the long wavelength component when the diagnostic part 10 is not exposed to the excitation light L1 is represented as follows.

$$If\lambda_1'' = I_{B1} + I_{B2}.$$

The subtracter 6c subtracts the apparent short wavelength component $If\lambda_1'$ when the diagnostic part 10 is not exposed to the excitation light L1 from the apparent short wavelength component $If\lambda_1'$ when the diagnostic part 10 is exposed to the excitation light L1 and obtains a net short wavelength component $If\lambda_1$. The net short wavelength component $If\lambda_1$ is represented as follows.

$$If\lambda_1 = k\lambda_1 \cdot I\lambda_{ex} \cdot \eta F\lambda_1 \cdot N \cdot \eta D$$

The subtracter 5c subtracts the sum fluorescence component $If\lambda''$ when the diagnostic part 10 is not exposed to the excitation light L1 from the sum fluorescence component $If\lambda'$ when the diagnostic part 10 is exposed to the excitation light L1 and obtains a net sum fluorescence component $If\lambda$. The net sum fluorescence component $If\lambda$ is represented as follows.

$$If\lambda = (k\lambda_1 \cdot I\lambda_{ex} \cdot \eta F\lambda_1 \cdot n \cdot \eta D) + (k\lambda_2 \cdot I\lambda_{ex} \cdot \eta F\lambda_2 \cdot N \cdot \eta D)$$

Then the divider means 7 divides the net short wavelength component $If\lambda_1$ by the net sum fluorescence component $If\lambda/(If\lambda_1 + If\lambda_2)$ That is, $$If\lambda/(If\lambda_1 + If\lambda_2) = (k\lambda_1 \cdot \eta F\lambda_1 \cdot N)/(k\lambda_1 \cdot I\lambda_{ex} \cdot \eta F\lambda_1 \cdot n + k\lambda_2 \cdot I\lambda_{ex} \cdot \eta F\lambda_2 \cdot N)$$

By this division, the term depending on the distance between the excitation light source 1a and the diagnostic part 10 is cancelled. In the manner described above, the intensity of fluorescence can be effectively corrected even there is a base line component.

Though the above description is made on the division of the short wavelength component by the sum fluorescence component, a division may be carried out on the long wavelength component (e.g., a red region component) and a sum fluorescence component (e.g., G+R). In this case, the above "short wavelength component" which is not a part of the sum fluorescence component should be reread as "long wavelength component".

Further a division may be carried out on a difference fluorescence component between a short wavelength component and a long wavelength component (e.g., G−R) and a sum fluorescence component (e.g., G+R). In this case, the above "short wavelength component" which is not a part of the sum fluorescence component should be reread as "difference fluorescence component".

Further though the above description is made on the case where the auto fluorescence emitted from the diagnostic part 10 which has not been given any fluorescence diagnosis agent is detected, this embodiment can be also applied when the extrinsic fluorescence emitted from the diagnostic part 10 which has been given a fluorescence diagnosis agent is detected. In this case, the above "long wavelength component" should be reread as "extrinsic fluorescence" and the above "short wavelength component" should be reread as "auto fluorescence", and the above "difference fluorescence component between the short wavelength component and the long wavelength component" should be reread as "difference fluorescence component (Ex-Ix) between the extrinsic component and the auto fluorescence component".

Now a description will be made on a case where auto fluorescence emitted from intrinsic pigment in the diagnostic part 10 upon excitation by the excitation light L1 without giving any fluorescence diagnosis agent to the diagnostic part 10 is detected and a division is carried out between a short wavelength component (e.g., a green component G) and a whole visible auto fluorescence component.

The auto fluorescence L3 emitted from the pigment in the diagnostic part 10 is separated into a short wavelength component and a whole visible auto fluorescence component by a dichroic mirror or the like and the first and second fluorescence detecting means 3 and 4 respectively detect the short wavelength component and the whole visible auto fluorescence component. The short wavelength component which the first fluorescence detecting means 3 detects when the excitation light L1 is projected onto the diagnostic part 10 is stored in the memory 5a and that the first fluorescence detecting means 3 detects when the excitation light L1 is intermitted is stored in the memory 5b. The whole visible auto fluorescence component which the second fluorescence detecting means 4 detects is when the excitation light L1 is projected onto the diagnostic part 10 is stored in the memory 6a and that the second fluorescence detecting means 4 detects when the excitation light L1 is intermitted is stored in the memory 6b.

The respective components detected by the first and second fluorescence detecting means 3 and 4 are represented as follows.

The apparent short wavelength component If$\lambda_1$' when the diagnostic part 10 is exposed to the excitation light L1:

$$If\lambda_1'=k\lambda_1 \cdot I\lambda_{ex} \cdot \eta F\lambda_1 \cdot N \cdot \eta D + I_{B1}.$$

The apparent whole visible auto fluorescence component If$\lambda_3$' when the diagnostic part 10 is exposed to the excitation light L1:

$$If\lambda_3'=k\lambda_3 \cdot I\lambda_{ex} \cdot \eta F\lambda_3 \cdot M \cdot \eta D + I_{B3}.$$

The apparent short wavelength component If$\lambda_1$" when the diagnostic part 10 is not exposed to the excitation light L1:

$$If\lambda_1''=I_{B1}.$$

The apparent whole visible auto fluorescence component If$\lambda_3$" when the diagnostic part 10 is not exposed to the excitation light L1:

$$If\lambda_3''=I_{B3}.$$

The subtracter 5c subtracts the apparent short wavelength component If$\lambda_1$" when the diagnostic part 10 is not exposed to the excitation light L1 from the apparent short wavelength component If$\lambda_1$' when the diagnostic part 10 is exposed to the excitation light L1 and obtains a net short wavelength component If$\lambda_1$. The net short wavelength component If$\lambda_1$ is represented as follows.

$$If\lambda_1=k\lambda_1 \cdot I\lambda_{ex} \cdot \eta F\lambda_1 \cdot N \cdot \eta D$$

The subtracter 6c subtracts the whole visible auto fluorescence component If$\lambda_3$" when the diagnostic part 10 is not exposed to the excitation light L1 from the whole visible auto fluorescence component If$\lambda_3$' when the diagnostic part 10 is exposed to the excitation light L1 and obtains a net whole visible auto fluorescence component If$\lambda_3$. The net whole visible auto fluorescence component If$\lambda_3$ is represented as follows.

$$If\lambda_3=k\lambda_3 \cdot I\lambda_{ex} \cdot \eta F\lambda_3 \cdot M \cdot \eta D$$

Then the divider means 7 divides the net short wavelength component If$\lambda_1$ by the net whole visible auto fluorescence component If$\lambda_1$/If$\lambda_3$. That is, $$If\lambda_1/If\lambda_3=(k\lambda_1 \cdot \eta F\lambda_1 \cdot N)/(k\lambda_3 \cdot I\lambda_{ex} \cdot \eta F\lambda_3 \cdot M)$$

By this division, the term depending on the distance between the excitation light source 1a and the diagnostic part 10 is cancelled. In the manner described above, the intensity of fluorescence can be effectively corrected even there is a base line component.

Though the above description is made on the division of the short wavelength component by the whole visible auto fluorescence component, a division may be carried out on the long wavelength component (e.g., a red region component) and a whole visible auto fluorescence component. In this case, the above "short wavelength component" which is not a part of the whole visible auto fluorescence component should be reread as "long wavelength component".

Further a division may be carried out on a difference fluorescence component between a short wavelength component and a long wavelength component (e.g., G–R) and a whole visible auto fluorescence component. In this case, the above "short wavelength component" which is not a part of the sum fluorescence component should be reread as "difference fluorescence component".

Further though the above description is made on the case where the auto fluorescence emitted from the diagnostic part 10 which has not been given any fluorescence diagnosis agent is detected, this embodiment can be also applied when the extrinsic fluorescence emitted from the diagnostic part 10 which has been given a fluorescence diagnosis agent is detected. In this case, the above "long wavelength component" should be reread as "extrinsic fluorescence" and the above "short wavelength component" should be reread as "auto fluorescence", and the above "difference fluorescence component between the short wavelength component and the long wavelength component" should be reread as "difference fluorescence component (Ex-Ix) between the extrinsic component and the auto fluorescence component".

Now an example of an endoscope system provided with a fluorescence diagnosis system in accordance with the present invention will be described with reference to FIGS. 3 to 6, hereinbelow. In this example, auto fluorescence emitted from intrinsic pigment in the diagnostic part 10 upon excitation by the excitation light L1 without giving any fluorescence diagnosis agent to the diagnostic part 10 is detected and a division is carried out between a green auto fluorescence component and a red auto fluorescence component.

Figure 3:
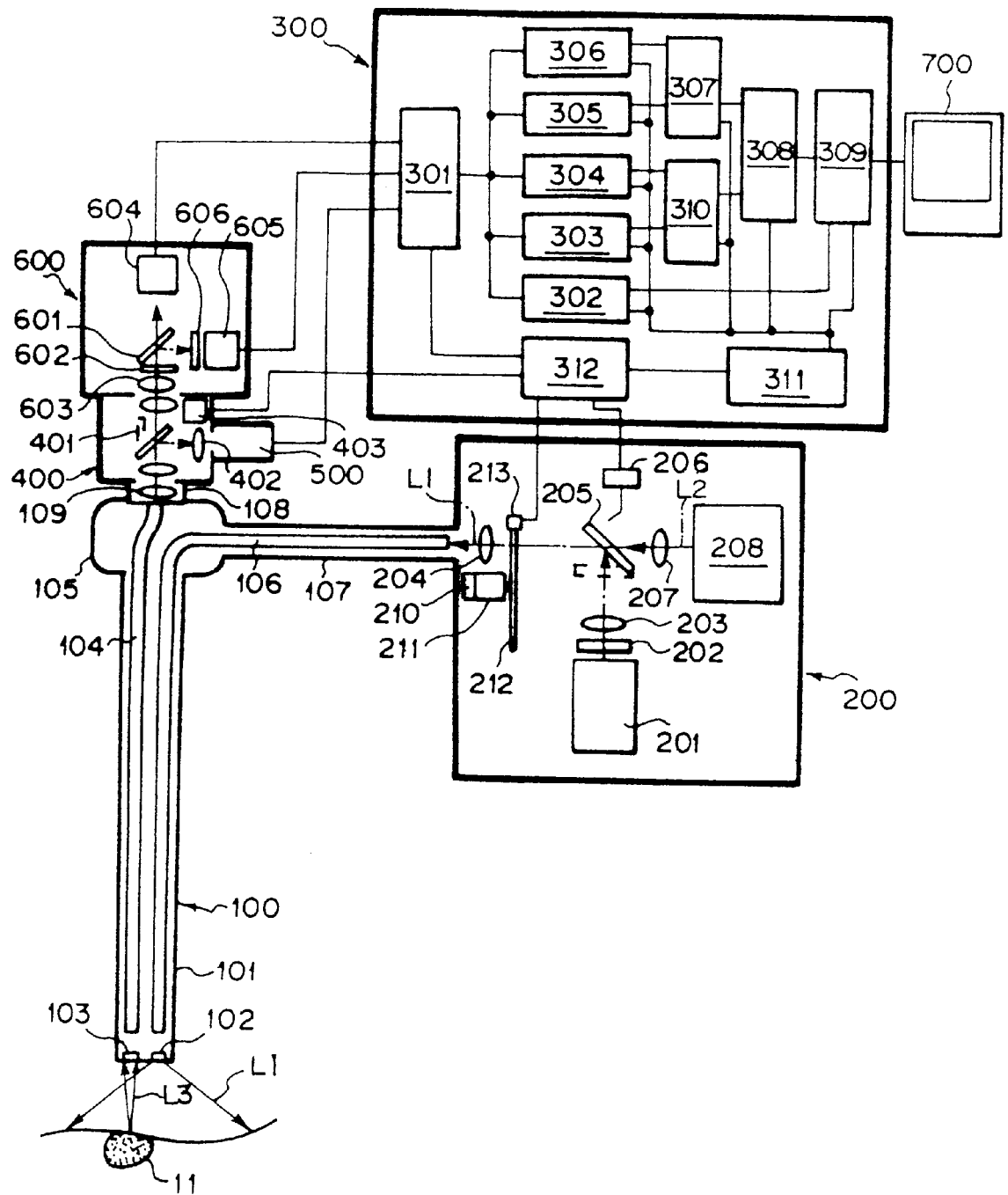
FIG. 3 is a schematic view showing an example of an endoscope system provided with a fluorescence detecting system in accordance with the present invention, FIGS. 4A to 4C respectively show the transmission characteristics of the first optical filter, the dichroic mirror and the second optical filter.
Figure 4A:
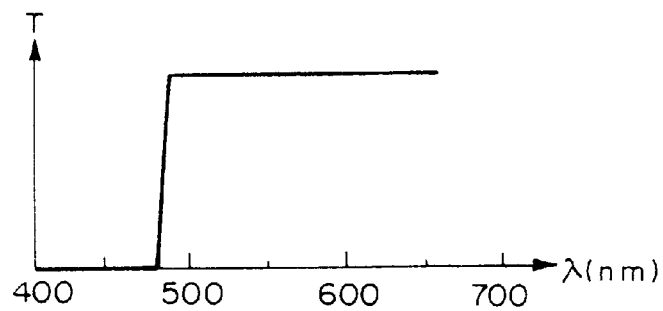
Figure 4B:
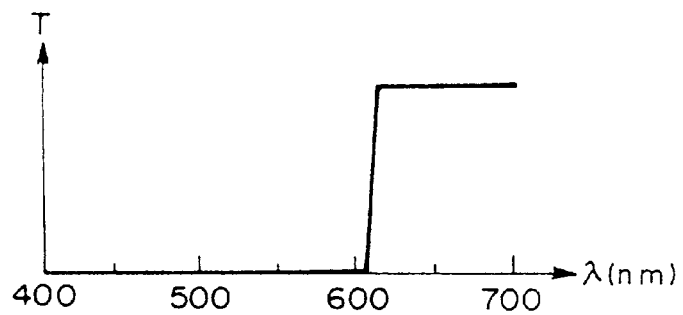
Figure 4C:
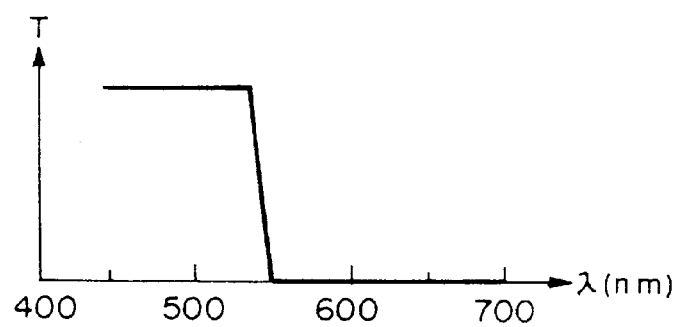

In FIG. 3, an endoscope system comprises an endoscope 100 which is inserted into a part of a patient which is to be observed, an illumination system 200 having an illuminating light source for emitting white illuminating light for a normal image and an excitation light source for emitting an excitation light, an optical path change-over unit 400 for switching the optical path between that for a normal image and that for a fluorescence image, a color CCD camera 500 which receives the white illuminating light reflected by the diagnostic part when a normal image is to be observed, a high speed camera unit 600 which receives fluorescence emitted from the diagnostic part upon excitation by the excitation light when a fluorescence image is to be observed, an image processing system 300 for processing the reflected light image or the fluorescence image, and a display 700 which reproduces the processed image information as a visible image.

The endoscope 100 comprises a light guide 106 and an image fiber 104 extending through an insertion portion 101 to the tip thereof. An illumination lens 102 and an objective lens 103 are disposed on the tip of the insertion portion 101. An end portion of the light guide 106 extends to the illumination system 200 through a connection 107 which connects a control section 105 and the illumination system 200. An end portion of the image fiber 104 extends to the control section 105 and is in contact with an eyepiece unit 108 having an eyepiece 109.

Figure 5:
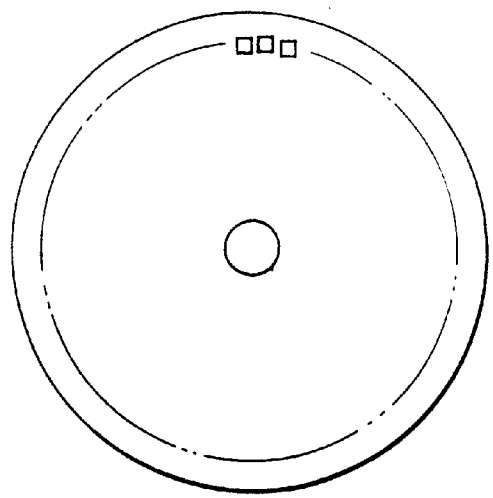
FIG. 5 is a plan view of the light chopper.

The illumination system 200 comprises a xenon lamp 208 which emits white light L2 for observing the normal image, a mercury-vapor lamp 201 which emits excitation light L1 for observing the fluorescence image, an optical filter 202 which transmits a selected wavelength range component of the excitation light L1 emitted from the mercury-vapor lamp 201, and a change-over mirror 205 which is driven by a driver 206 to selectively introduce the white light L2 or the excitation light L1 to the light guide 106. The illumination system 200 further comprises a light chopper 212 which intermits the excitation light L1 driven by a motor 211, an electromagnetic brake 210 which stops the light chopper 212 in a desired position and a position sensor 213 which detects the position of perforations in the light chopper 212. As shown in FIG. 5, the light chopper 212 is provided with a plurality of perforations and when the light chopper 212 is rotated, the excitation light L1 is intermittently projected to the diagnostic part 10 through the perforations.

The optical path change-over unit 400 is provided with a change-over mirror 401 which is driven by a driver 403 to selectively connect the image fiber 104 to the color CCD camera 500 or the high speed camera unit 600 so that the reflected light transmitted through the image fiber 104 is led to the CCD camera 500 when a normal image is to be observed and the fluorescence L3 transmitted through the image fiber 104 is led to the high speed camera unit 600 when a fluorescence image is to be observed.

The high speed camera unit 600 comprises an optical filter 602 for cutting the excitation light component, and a dichroic mirror 601 which separates the fluorescence L3 passing through the optical filter 602 in a red region component and a green region component so that the red region component is focused on a high speed camera 604 and the green region component is focused on a high speed camera 605.

The image processing system 300 comprises an A/D convertor 301 which digitizes image signals from the color CCD camera 500 and the high speed cameras 604 and 605, a normal image memory 302 which stores the digitized normal image signal, a green background light image memory 303 which stores a digitized image signal bearing thereon a fluorescence image taken by the high speed camera 605 when the excitation light L1 is intermitted, a green fluorescence image memory 304 which stores a digitized image signal bearing thereon a fluorescence image taken by the high speed camera 605 when the excitation light L1 is projected, a red background light image memory 305 which stores a digitized image signal bearing thereon a fluorescence image taken by the high speed camera 604 when the excitation light Li is intermitted, a red fluorescence image memory 306 which stores a digitized image signal bearing thereon a fluorescence image taken by the high speed camera 604 when the excitation light L1 is projected, a red difference image memory 307 which subtracts the output of the red background light image memory 305 from the output of the red fluorescence image memory 306 and stores the result of the subtraction, a green difference image memory 310 which subtracts the output of the green background light image memory 303 from the output of the green fluorescence image memory 304 and stores the result of the subtraction,
  a divider memory 308 which divides the output of the green difference image memory 310 by the output of the red difference image memory 307 and stores the result of the division, a video signal generating circuit 309 which carries out an image processing on the image signals stored in the normal image memory 302 and the divider memory 308 in order to display a visible image on a display 700 on the basis of the image signals, a timing controller 312 which controls the drivers 206 and 403 and the A/D convertor 301, and a video processor 311 which controls memories 302 to 308 and 310 and the video signal generating circuit 309.

Operation of the endoscope system will be described hereinbelow.

When a normal image is to be observed, the change-over mirror 205 is moved by the driver 206 under the control of a signal from the timing controller 312 to the position shown by the broken line, where it permits the white light L2 from the xenon lamp 208 to pass through. The white light L2 emitted from the xenon lamp 208 travels through a lens 207 toward the light chopper 212. At this time the light chopper 212 is stopped with a perforation held in the optical path of the white light L2. Accordingly the white light L2 passes the light chopper 212 through the perforation and is caused to enter the light guide 106 by a lens 204. The white light L2 propagates through the light guide 106 and emanates from the front end of the light guide 106 to illuminate the diagnostic part 10 including the diseased part 11 through an illuminator lens 102.

A part of the white light L2 reflected by the diagnostic part 10 is condensed by the objective lens 103 and travels toward the change-over mirror 401 in the change-over unit 400 through the image fiber 104 and the eyepiece 109 of the eyepiece unit 108.

The change-over mirror 401 is driven by the driver 403 under the control of a signal from the timing controller 312 and is moved to the position shown by the solid line when a normal image is to be observed. The reflected light is reflected by the mirror 401 and focused on the color CCD camera 500 by a lens 402.

The red, green and blue image signals from the color CCD camera 500 are input into the A/D convertor 301 and digitized. The digitized red, green and blue image signals are stored in the corresponding normal image memories 302. The normal image signals stored in the normal image memories 302 are subjected to a color matrix processing and an encoding processing after D/A conversion by the video signal generating circuit 309, and then input into the display 700 as NTSC signals to be reproduced as a visible image by the display 700. The aforesaid series of actions are carried out under the control of the video processor 311 and the timing controller 312.

When a fluorescence image is to be observed, the change-over mirror 205 is moved by the driver 206 under the control of a signal from the timing controller 312 to the position shown by the solidine, where it cuts the white light L2 and reflects the excitation light L1. The excitation light L1 emitted from the mercury-vapor lamp 201 travels through the optical filter 202 and a lens 203 to impinge upon the change-over mirror 205. The excitation light L1 reflected by the change-over mirror 205 travels toward the light chopper 212. At this time the light chopper 212 is rotated and intermittently cuts the excitation light L1. The intermittent excitation light L1 is caused to enter the light guide 106 by the lens 204 and propagates through the light guide 106. Then the intermittent excitation light L1 emanates from the front end of the light guide 106 and is projected onto the diagnostic part 10 including the diseased part 11 by the illuminator lens 102. The optical filter 201 transmits a bright-line spectrum having a central wavelength of 405 nm.

Fluorescence L3 emitted by the diagnostic part 10 upon excitation by the excitation light L1 is condensed by the objective lens 103 and travels toward the change-over mirror 401 in the change-over unit 400 through the image fiber 104 and the eyepiece 109 of the eyepiece unit 108.

The change-over mirror 401 is driven by the driver 403 under the control of a signal from the timing controller 312 and is moved to the position shown by the broken line not to interrupt the fluorescence L3. The fluorescence L3 passes by the mirror 403 and travels toward the dichroic mirror 601 through a lens 603 and an optical filter 602. The optical filter has transmission characteristics shown in FIG. 4A and transmits only fluorescence having wavelengths not shorter than 480 nm. Accordingly the excitation light L1 whose central wavelength is 405 nm is cut. The dichroic mirror 601 has transmission characteristics shown in FIG. 4B and a red region component having a wavelength not shorter than 610 nm passes through the dichroic mirror 601 to impinge upon the high speed camera 604 and a fluorescence component having a wavelength shorter than 610 nm is reflected by the dichroic mirror 601 toward the high speed cam era 605. The fluorescence component reflected by the dichroic mirror 601 impinges upon an optical filter 606 which has transmission character is tics shown in FIG. 4C. Thus only a green region component having a wavelength in the range of 480 nm to 540 nm can impinge upon the high speed camera 605.

Figure 6:
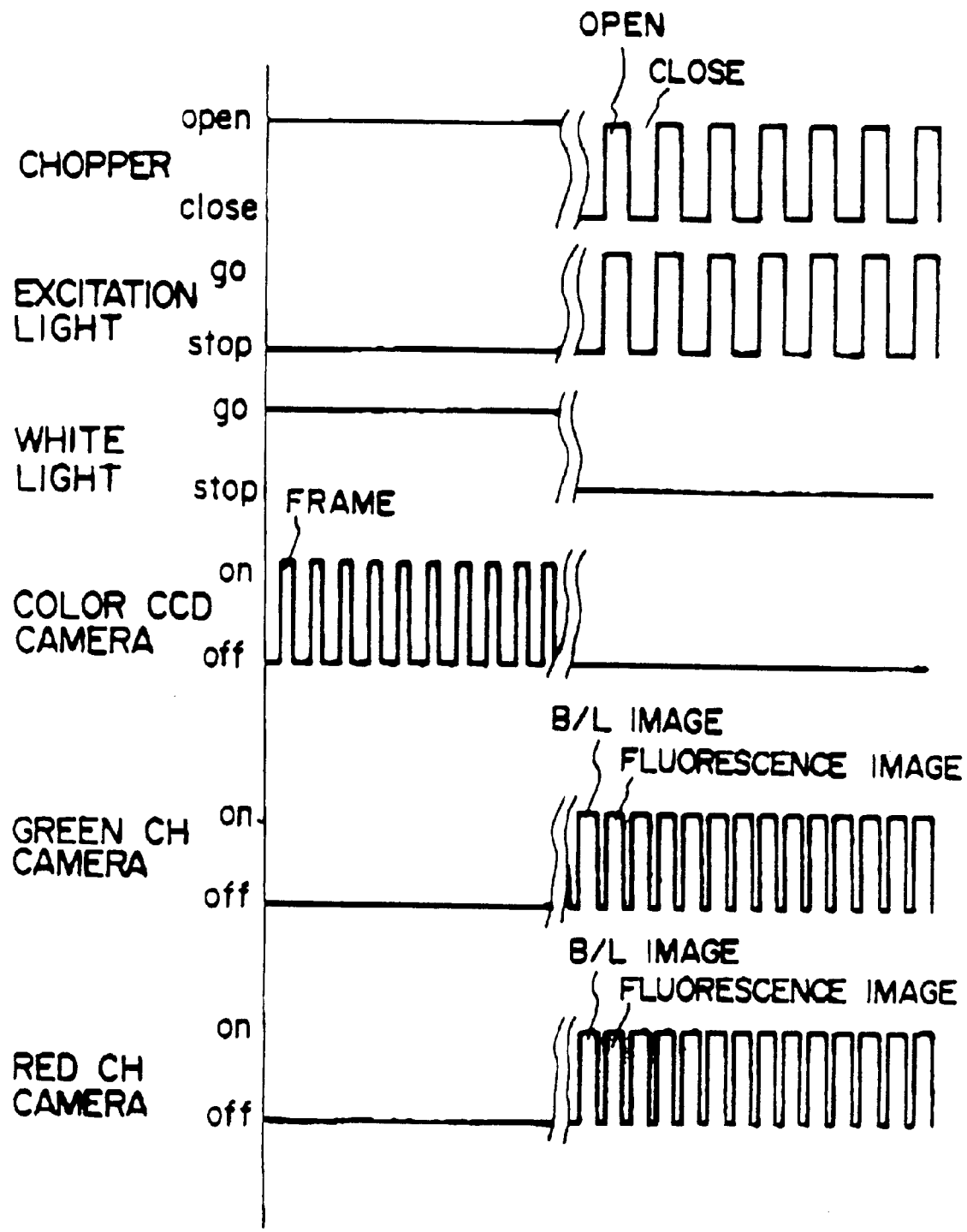
FIG. 6 is a timing chart of the endoscope system.

The light chopper 212, the excitation light L1, the color CCD camera 500 and the high speed cameras 604 and 605 are controlled by the video processor 311 and the timing controller 312. FIG. 6 shows a timing chart for these elements. When a fluorescence image is to be observed, the high speed camera 604 (red channel) and the high speed camera 604 (green channel) are driven in response to turning on and off of the excitation light L1.

The image signals obtained by the high speed camera 604 respectively bearing thereon a fluorescence image when the excitation light L1 is projected and a background light image when the excitation light L1 is cut are digitized by the A/D convertor 301. The digitized fluorescence image signal is stored in the red fluorescence image memory 306 and the digitized background light image signal is stored in the red background light image memory 305. Then the output of the red background light image memory 305 is subtracted from the output of the red fluorescence image memory 306 and a red difference image signal is stored in the red difference image memory 307.

Similarly, the image signals obtained by the high speed camera 605 respectively bearing thereon a fluorescence image when the excitation light L1 is projected and a background light image when the excitation light L1 is cut are digitized by the A/D convertor 301. The digitized fluorescence image signal is stored in the green fluorescence image memory 304 and the digitized background light image signal is stored in the green background light image memory 303. Then the output of the green background light image memory 303 is subtracted from the output of the green fluorescence image memory 304 and a green difference image signal is stored in the green difference image memory 310.

The divider memory 308 divides the output of the green difference image memory 310 by the output of the red difference image memory 307 and the divided image signal is stored in the divider memory 308.

The divided image signal stored in the divider memory 308 is subjected to an encoding processing by the video signal generating circuit 309 after D/A conversion and then input into the display 700 to be reproduced as a visible image by the display 700. The normal image and the divided image may be overlaid.

Further though, in the embodiment described above, the fluorescence detecting system in accordance with the present invention is applied to an image taking system, the present invention can be applied also to an optical scanning system. In this case, fluctuation in the detecting efficiency ηD depending upon the distance between the light emitting point and the photodetector can be cancelled.

What is claimed is:

1. A fluorescence detecting system for detecting auto fluorescence emitted from an intrinsic pigment in a part of an organism to be observed comprising:

an excitation light projecting means which intermittently projects onto the part to be observed excitation light in a wavelength range which can excite the intrinsic pigment of the organism to emit auto fluorescence, a fluorescence detecting means which extracts an auto fluorescence component in a desired wavelength range from auto fluorescence emitted from the intrinsic pigment, a base line component removing means which obtains a net auto fluorescence component in the desired wavelength range by subtracting a base line component in the desired wavelength range the fluorescence detecting means detects when the part of the organism is not exposed to the excitation light from a gross auto fluorescence component in the desired wavelength range the fluorescence detecting means detects when the part of the organism is exposed to the excitation light, and a divider means which carries out a division between a first part of the net auto fluorescence component in the desired wavelength range and a second part of the net auto fluorescence component in the desired wavelength range.

2. A fluorescence detecting system as defined in claim 1 in which said fluorescence detecting means detects a whole visible auto fluorescence component in a visible region having a predetermined wavelength range including a first relatively short wavelength range and a first relatively long wavelength range, and one of an auto fluorescence component in a second relatively short wavelength range, an auto fluorescence component in a second relatively long wavelength range and a difference fluorescence component between the auto fluorescence components in said second relatively short wavelength range and in said second relatively long wavelength range, and said first part of the net auto fluorescence component is obtained from one of said auto fluorescence components or from the difference fluorescence component, and said second part of the net auto fluorescence component is obtained from the whole visible auto fluorescence component.

3. A fluorescence detecting system as defined in claim 1 in which said fluorescence detecting means detects a sum fluorescence component in an auto fluorescence component in a first short wavelength range and an auto fluorescence component in a first relatively long wavelength range, and one of an auto fluorescence component in a second relatively short wavelength range, an auto fluorescence component in a second relatively long wavelength range and a difference fluorescence component between the auto fluorescence components in said second relatively short wavelength range and in said second relatively long wavelength range, and said first part of the net auto fluorescence component is obtained from one of said auto fluorescence components, or from the difference fluorescence component, and said second part of the net auto fluorescence component is obtained from the sum auto fluorescence component.

4. A fluorescence detecting system as defined in claim 1 in which said fluorescence detecting means two-dimensionally detects the auto fluorescence emitted from the part to be observed and obtains a fluorescence image of the part.

5. A fluorescence detecting system as defined in claim 1 in which said fluorescence detecting means detects said auto fluorescence component in a relatively short wavelength range and said auto fluorescence component in a relatively long wavelength range, and said first part is said fluorescence component in the relatively long wavelength range and said second part is said fluorescence component in the relatively short wavelength range.

6. A fluorescence detecting system for detecting fluorescence emitted from a part of an organism to be observed which has been given a fluorescent photosensitive material comprising:

an excitation light projecting means which intermittently projects onto the part to be observed excitation light in a wavelength range which can excite an intrinsic pigment of the organism and said fluorescent photosensitive material to emit fluorescence, a fluorescence detecting means which extracts a fluorescence component in a desired wavelength range from fluorescence emitted from the intrinsic pigment and the fluorescent photosensitive material, a base line component removing means which obtains a net fluorescence component in the desired wavelength range by subtracting a base line component in the desired wavelength range the fluorescence detecting means detects when the part of the organism is not exposed to the excitation light from a gross fluorescence component in the desired wavelength range which the fluorescence detecting means detects when the part of the organism is exposed to the excitation light, and a divider means which carries out a division between a first part of the net fluorescence component in the desired wavelength range and a second part of the net fluorescence component in the desired wavelength range.

7. A fluorescence detecting system as defined in claim 6 in which said fluorescence detecting means detects a whole visible fluorescence component in a visible region having a predetermined wavelength range including a first wavelength range of extrinsic fluorescence emitted from the photosensitive material and a first wavelength range of auto fluorescence emitted from the intrinsic pigment and one of a fluorescence component in a second wavelength range of the extrinsic fluorescence, a fluorescence component in a second wavelength range of the auto fluorescence or a difference fluorescence component between the fluorescence components in said second wavelength range of the extrinsic fluorescence and in said second wavelength range of the auto fluorescence, and said first part of the net fluorescence component is obtained from said fluorescence component in a second wavelength range of the extrinsic fluorescence, said fluorescence component in a second wavelength range of the auto fluorescence, or said difference fluorescence component, and said second part of the net fluorescence component is obtained from the whole visible fluorescence component.

8. A fluorescence detecting system as defined in claim 6 in which said fluorescence detecting means detects a sum fluorescence component in a first wavelength range of extrinsic fluorescence emitted from the photosensitive material and fluorescence component in a first wavelength range of auto fluorescence emitted from the intrinsic pigment and one of a fluorescence component in a second wavelength range of the extrinsic fluorescence, a fluorescence component in a second wavelength range of the auto fluorescence or a difference fluorescence component between the fluorescence components in said second wavelength range of the extrinsic fluorescence and in said second wavelength range of the auto fluorescence, and said first part of the net fluorescence component is obtained from said fluorescence component in a second wavelength range of the extrinsic fluorescence, said fluorescence component in a second wavelength range of the auto fluorescence, or said difference fluorescence component, and said second part of the net fluorescence component is obtained from the sum fluorescence component.

9. A fluorescence detecting system as defined in claim 6 in which said fluorescence detecting means two-dimensionally detects the auto fluorescence emitted from the part to be observed and obtains a fluorescence image of the part.

10. A fluorescence detecting system as defined in claim 6 in which said fluorescence detecting means detects extrinsic fluorescence emitted from the photosensitive material and auto fluorescence emitted from the pigment, and said first part is the auto fluorescence emitted from the pigment and second part is the extrinsic fluorescence emitted from the photosensitive material.

11. A fluorescence detecting system for detecting auto fluorescence emitted from an intrinsic pigment in a part of an organism to be observed comprising:

an excitation light projector which intermittently projects excitation light onto the part of the organism to be observed in a wavelength range which can excite the intrinsic pigment of the organism to emit auto fluorescence, a fluorescence detector which extracts an auto fluorescence component in a desired wavelength range from the auto fluorescence emitted from the intrinsic pigment and outputs a first signal, a base line component removing circuit comprising a subtractor which inputs a second signal when the organism is not exposed to said excitation light, said second signal defined as a base line component, and which inputs said first signal when the organism is exposed to said excitation light, and which takes the difference of the first and second signals, and thereby obtains a net auto fluorescence component in the desired wavelength range, and a divider which carries out a division between a first part of the net auto fluorescence component in the desired wavelength range and a second part of the net auto fluorescence component in the desired wavelength range.

12. A fluorescence detecting system as defined in claim 11 in which said fluorescence detector detects a whole visible auto fluorescence component in a visible region having a predetermined wavelength range including a first relatively short wavelength range and a first relatively long wavelength range, and one of an auto fluorescence component in a second relatively short wavelength range, an auto fluorescence component in a second relatively long wavelength range and a difference fluorescence component between the auto fluorescence components in said second relatively short wavelength range and in said second relatively long wavelength range, and said first part of the net auto fluorescence component is obtained from one of said auto fluorescence components, or from the difference fluorescence component, and said second part of the net auto fluorescence component is obtained from the whole visible auto fluorescence component.

13. A fluorescence detecting system as defined in claim 11 in which said fluorescence detector detects a sum fluorescence component in an auto fluorescence component in a first short wavelength range and an auto fluorescence component in a first relatively long wavelength range, and one of an auto fluorescence component in a second relatively short wavelength range, an auto fluorescence component in a second relatively long wavelength range and a difference fluorescence component between the auto fluorescence components in said second relatively short wavelength range and in said second relatively long wavelength range, and said first part of the net auto fluorescence component is obtained from one of said auto fluorescence components, or from the difference fluorescence component, and said second part of the net auto fluorescence component is obtained from the sum auto fluorescence component.

14. A fluorescence detecting system as defined in claim 11 in which said fluorescence detector two-dimensionally detects the auto fluorescence emitted from the part to be observed and obtains a fluorescence image of the part.

15. A fluorescence detecting system as defined in claim 11 in which said fluorescence detector detects extrinsic fluorescence emitted from the photosensitive material and auto fluorescence emitted from the pigment, and said first part is the auto fluorescence emitted from the pigment and said second part is the extrinsic fluorescence emitted from the photosensitive material.

16. A fluorescence detecting system for detecting fluorescence emitted from a part of an organism to be observed which has been given a fluorescent photosensitive material comprising an excitation light projector which intermittently projects excitation light onto the part of the organism to be observed in a wavelength range which can excite an intrinsic pigment of the organism and said fluorescent photosensitive material to emit fluorescence, a fluorescence detector which extracts a fluorescence component in a desired wavelength range from fluorescence emitted from the intrinsic pigment as well as the fluorescent photosensitive material, and outputs a first signal, a base line component removing circuit comprising a subtractor which inputs a second signal when the organism is not exposed to said excitation light, said second signal defined as a base line component, and which inputs said first signal when the organism is exposed to said excitation light, and which takes the difference of the first and second signals, and thereby obtains a net auto fluorescence component in the desired wavelength range, and a divider which carries out a division between a first part of the net auto fluorescence component in the desired wavelength range and a second part of the net auto fluorescence component in the desired wavelength range.

17. A fluorescence detecting system as defined in claim 16 in which said fluorescence detector detects a whole visible auto fluorescence component in a visible region having a predetermined wavelength range including a first wavelength range of extrinsic fluorescence emitted from the photosensitive material and a first wavelength range of auto fluorescence emitted from the intrinsic pigment and one of a fluorescence component in a second wavelength range of the extrinsic fluorescence, a fluorescence component in a second wavelength range of the auto fluorescence, or a difference fluorescence component between the fluorescence components in said second wavelength range of the extrinsic fluorescence and in said second wavelength range of the auto fluorescence, and said first part of the net fluorescence component is obtained from said fluorescence component in a second wavelength range of the extrinsic fluorescence, said fluorescence component in a second wavelength range of the auto fluorescence, or said difference fluorescence component, and said second part of the net fluorescence component is obtained from the whole visible fluorescence component.

18. A fluorescence detecting system as defined in claim 16 in which said fluorescence detect a sum fluorescence component in a first wavelength range of extrinsic fluorescence emitted from the photosensitive material and fluorescence component in a first wavelength range of auto fluorescence emitted from the intrinsic pigment and one of a fluorescence component in a second wavelength range of the extrinsic fluorescence, a fluorescence component in a second wavelength range of the auto fluorescence, or a difference fluorescence component between the fluorescence components in said second wavelength range of the extrinsic fluorescence and in said second wavelength range of the auto fluorescence, and said first part of the net fluorescence component is obtained from said fluorescence component in a second wavelength range of the extrinsic fluorescence, said fluorescence component in a second wavelength range of the auto fluorescence, or said difference fluorescence component, and said second part of the net fluorescence component is obtained from the sum fluorescence component.

19. A fluorescence detecting system as defined in claim 16 in which said fluorescence detector two-dimensionally detects the fluorescence emitted from the part to be observed and obtains a fluorescence image of the part.

20. A fluorescence detecting system as defined in claim 16 in which said fluorescence detector detects said auto fluorescence component in a relatively short wavelength range and said auto fluorescence component in a relatively long wavelength range, and said first part is said fluorescence component in the relatively long wavelength range and said second part is said fluorescence component in the relatively short wavelength range.

* * * * *